US010975400B2

(12) United States Patent
Zheng et al.

(10) Patent No.: US 10,975,400 B2
(45) Date of Patent: Apr. 13, 2021

(54) 5-AMINOLEVULINIC ACID HIGH-YIELD BACTERIAL STRAIN, PREPARATION METHOD AND USE THEREOF

(71) Applicant: Tianjin Institute of Industrial Biotechnology, Chinese Academy of Sciences, Tianjin (CN)

(72) Inventors: Ping Zheng, Tianjin (CN); Jiuzhou Chen, Tianjin (CN); Wei Pu, Tianjin (CN); Jibin Sun, Tianjin (CN); Xinyang Wu, Tianjin (CN); Yanhe Ma, Tianjin (CN)

(73) Assignee: Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 0 days.

(21) Appl. No.: 14/766,020

(22) PCT Filed: Jan. 28, 2014

(86) PCT No.: PCT/CN2014/071712
§ 371 (c)(1),
(2) Date: Aug. 5, 2015

(87) PCT Pub. No.: WO2014/121724
PCT Pub. Date: Aug. 14, 2014

(65) Prior Publication Data
US 2015/0376661 A1 Dec. 31, 2015

(30) Foreign Application Priority Data
Feb. 7, 2013 (CN) .......................... 201310051018.X

(51) Int. Cl.
| | | |
|---|---|---|
| *C12N 1/21* | (2006.01) | |
| *C12N 9/88* | (2006.01) | |
| *C12N 9/90* | (2006.01) | |
| *C12P 13/00* | (2006.01) | |
| *C12N 9/10* | (2006.01) | |
| *C12N 9/04* | (2006.01) | |
| *C12N 9/02* | (2006.01) | |
| *C12N 9/00* | (2006.01) | |

(52) U.S. Cl.
CPC ............ *C12P 13/001* (2013.01); *C12N 9/001* (2013.01); *C12N 9/0006* (2013.01); *C12N 9/88* (2013.01); *C12N 9/93* (2013.01); *C12P 13/005* (2013.01); *C12Y 101/01038* (2013.01); *C12Y 203/01037* (2013.01); *C12Y 401/01031* (2013.01); *C12Y 401/01049* (2013.01)

(58) Field of Classification Search
None
See application file for complete search history.

(56) References Cited

U.S. PATENT DOCUMENTS 6,455,284 B1 * 9/2002 Gokarn .................... C12N 9/88
435/41

FOREIGN PATENT DOCUMENTS

| CN | 101063104 A | 10/2007 | |
|---|---|---|---|
| CN | 101278041 A | 10/2008 | |
| CN | 102206606 A | 10/2011 | |
| JP | 2002511250 A | 4/2002 | |
| JP | 2003503064 A | 1/2003 | |
| JP | 2008513023 A | 5/2008 | |
| JP | 2012518999 A | 8/2012 | |
| JP | 2012522515 A | 9/2012 | |
| WO | WO 2007019301 A2 * | 2/2007 | ........... C07K 14/285 |
| WO | 2012/177943 A1 | 12/2012 | |

OTHER PUBLICATIONS

Shin et al., 5-Aminolevulinic Acid Biosynthesis in *Escherichia coli* Coexpressing NADP-dependent Malic Enzyme and 5-Aminolevulinate Synthase, J. Microbiol. Biotechnol., 2007, 17, 1579-84.*
Kind et al., Increased lysine production by flux coupling of the tricarboxylic acid cycle and the lysine biosynthetic pathway—Metabolic engineering of the availability of succinyl-CoA in *Corynebacterium glutamicum*, Metabolic Eng., Aug. 2, 2012, 15, 184-95.*
Millard et al., Enhanced Production of Succinic Acid by Overexpression of Phosphoenolpyruvate Carboxylase in *Escherichia coli*, Appl. Environmental Microbiol., 1996, 62, 1808-10.*
Lin et al., Metabolic engineering of aerobic succinate production systems in *Escherichia coli* to improve process productivity and achieve the maximum theoretical succinate yield, Metabolic Eng., 2005, 7, 116-27.*
Liu et al., Quantification and analysis of metabolic characteristics of aerobic succinate-producing *Escherichia coli* under different aeration conditions Process Biochemistry, 2012, 47, 1532-38.*
Lin et al., Characerization of 5-aminolevulinate synthase from *Agrobacterium radiobactor*, Bioresource Tech., 100, 2009, 2293-97.*
Xie et al., Optimization of recombinant aminolevulinate synthase production in *Escherichia coli* using factorial design, Appl Microbiol Biotechnol, 2003, 63, 267-273. (Year: 2003).*

(Continued)

*Primary Examiner* — Robert B Mondesi
*Assistant Examiner* — Todd M Epstein
(74) *Attorney, Agent, or Firm* — Kilpatrick Townsend and Stockton LLP

(57) ABSTRACT

A method for constructing an ALA production bacterial strain, the method enhances the activity of related enzymes promoting the synthesis of oxaloacetate and in the 5-aminolevulinic acid (ALA) production bacterial strain, or introducing exogenous related enzymes promoting the synthesis of oxaloacetate, such as phosphoenolpyruvate carboxylase or pyruvate carboxylase, and/or reducing the activity of related enzymes in the downstream metabolic pathway of succinyl coenzyme A in the bacterial strain, such as succinyl coenzyme A synthetase or succinate dehydrogenase, and/or reducing the activity of phosphoenolpyruvate carboxylated kinase and/or malic enzyme. An ALA high-yield bacterial strain constructed by utilizing the method, and method for utilizing the bacterial strain to prepare ALA.

6 Claims, 3 Drawing Sheets

Specification includes a Sequence Listing.

(56) References Cited

OTHER PUBLICATIONS

English Translation of International Search Report corresponding to PCT/CN2014/071712 dated May 20, 2014 (3 pages).
Correa Garcia, S. et al., "The Role of ALA-S and ALA-D in Regulating Porphyrin Biosynthesis in a Normal and a HEM R + Mutant Straing of *Saccharomyces cerevisiae*," Yeast (Dec. 1993) 9(31):165-173.
Fu, Weiqi, "Study on optimization and fermentation process regulation in the product of 5-Aminolevulinate recombinant strains," *China Doctoral Dissertations Full-Text Database* (Apr. 30, 2010), 139 pages.
Pu, Wei et al., "Deficiency of succinic dehydrogenase or succinyl-CoAsynthetase enhances the production of 5-aminolevulinic acid in recombinant *Escherichia coli*," *Chinese Journal of Biotechnology* (Oct. 25, 2013) 10(29):1494-1503.
Mizuno, Y. et al.; "Altered acetylation and succinylation profiles in *Corynebacterium glutamicum* in response to conditions inducing glutamate overproduction"; MicrobiologyOpen 2016; vol. 5, No. 1; pp. 152-173; John Wiley & Sons Ltd.
Petersen, S. et al.; "Metabolic Consequences of Altered Phosphoenolpyruvate Carboxykinase Activity in *Corynebacterium glutamicum* Reveal an aplerotic Regulation Mechanisms in Vivo"; Metabolic Engineering 3, pp. 344-361; 2001.
Peters-Wendisch, P.G. et al.; "Pyruvate Carboxylase is a Major Bottleneck for Glutamate and Lysine Production by *Corynebacterium glutamicum*"; J. Mol. Microbiol. Biotechnol.; vol. 3, No. 2; 2001; pp. 295-300; Horizon Scientific Press.
Schultz, C.; "Glutamate production by *Corynebacterium glutamicum*: dependence on the oxoglutarate dehydrogenase inhibitor protein Odhl and protein kinase PknG"; Appl. Microbiol. Biotechnol.; vol. 76; 2007; pp. 691-700.
Zhang, X. et al.; "Reengineering *Escherichia coli* for Succinate Production in Mineral Salts Medium"; Applied and Environmental Microbiology; vol. 75, No. 24; Dec. 2009; pp. 7807-7813; American Society for Microbiology.
Kang, Z et al.; "Metabolic engineering to improve 5-aminolevulinic acid production"; Bioengineered Bugs; vol. 2, No. 6; Nov./Dec. 2011; pp. 1-4.
Lin, H. et al.; "Increasing the Acetyl-CoA Pool in the Presence of Overexpressed Phosphoenolpyruvate Carboxylase or Pyruvate Carboxylase Enhances Succinate Productions in *Escherichia coli*"; Biotechnol. Prog.; vol. 20; 2004; pp. 1599-1604.
Marrs, B. et al.; "Regulation of Bacteriochlorophyll Synthesis by Oxygen in Respiratory Mutants of *Rhodopseudomonas capsulate*"; Journal of Bacteriology; vol. 114; Jun. 1973; pp. 1052-1057.

\* cited by examiner

5-AMINOLEVULINIC ACID HIGH-YIELD BACTERIAL STRAIN, PREPARATION METHOD AND USE THEREOF

REFERENCE TO SUBMISSION OF A SEQUENCE LISTING AS A TEXT FILE

The Sequence Listing written in file Sequence_listing.txt created on Aug. 4, 2015, 5,063 bytes, machine format IBM-PC, MS-Windows operating system, is hereby incorporated by reference in its entirety for all purposes.

TECHNICAL FIELD

The present invention relates to the field of genetic engineering and microbial fermentation. In particular, the present invention relates to a 5-aminolevulinic acid high-yield strain and a preparation method and use thereof.

BACKGROUND 5-aminolevulinic acid (ALA) is a precursor for synthesizing tetrapyrrole compounds, such as heme, chlorophyll, vitamin B12, in an organism, and tetrapyrrole compounds are important components for cytochromes, hemoglobin, and chloroplast protein, which play an important role in life activities. ALA is widely used in medicine, agriculture, animal husbandry, commodity chemicals and other areas, and is an important high-value-added bio-based chemical, due to its advantages, such as biodegradability, nontoxicity and no residues. ALA can be used in cancer therapy, tumor diagnosis and treatment of skin diseases as a new generation of photodynamics drugs; can be used to significantly promote the growth of flowers, plants and vegetables, and raise the quality of crops, fruits, and vegetables as plant growth regulators; and ALA can be used to enhance metabolism and immunity of animals as animal feed additives. Recently, ALA is also used as a main additive ingredient in the development of cosmetics and healthcare food, and relevant products have been marketed.

However, at present, ALA is mainly prepared by chemical synthesis, and there are some shortcomings such as multiple reaction steps, low conversion-rate, high production cost, high energy and material consumption, toxic raw materials used during the preparation, severe environmental pollution and high price. Currently, on the Chinese market, the producer price for ALA hydrochloride is about 17,000-19,000 RMB/kg, while the reagent grade price is up to 2,000 RMB/gm. High manufacturing cost has become a limiting factor in ALA application.

With the development of society and science and technology, replacing chemical synthesis by clean and efficient fermentation methods for producing ALA has become the focus of research. At present, the methods for producing ALA by, using microorganisms are generally two types: the first one is that photosynthetic bacteria is mutated for breeding high-yielding ALA mutants and the obtained mutant is cultured in a specific medium for accumulating high concentrations of ALA, however, the fermentation period of such method is relatively long, the controlling conditions are complex, and the addition of substrates and inhibitors will increase the production cost. The second one is that the metabolic pathway of a microorganism is modified through metabolic engineering, and an excess accumulation of ALA is achieved by strengthening ALA synthesis. In microorganisms, there are mainly two pathways for synthesizing ALA, one of which is C4 pathway, wherein ALA is synthesized by ALA synthetase using succinyl CoA and glycine as precursors; another one of which is C5 pathway, wherein ALA is synthesized by using glutamyl tRNA as precursor through a two-step reaction. Xie et al (Xie L, Hall D, Eiteman MA, Altman E, Appl Microbiol Biotechnol, 2003, 63 (3): 267-273) reported that 5.2 g/L of ALA yield can be obtained by using wild type *E. coli* MG1655 expressing ALA synthetase from *Rhodobacter sphaeroides* and through optimization of fermentation conditions. Jianping Lin et al., (CN200710068168.6, CN201210013562.0) reported that 6.6 g/L of ALA yield can be obtained by expressing ALA synthetase gene from *Rhodobacter sphaeroides* in *E. coli* Rosetta 2 (DE3) through optimization of fermentation process, and upon further optimization, 9.4 g/L of ALA yield can be obtained in a 15 L fermentor, which is the highest yield reported in the literature. All of the above studies focused on a relatively simple C4 pathway, and the effects are achieved mainly by expressing exogenous ALA synthetase in *E. coli* and adding in an enriched LB medium substrates (succinic acid and glycine) and inhibitors of downstream metabolic pathways. Higher level of ALA yield has been obtained by the above methods, however, the control of fermentation process is complex due to the use of LB medium and addition of substrates and inhibitors, and the production costs are increased, thereby limiting the large-scale industrial applications. Shin et al (Shin J A, Kwon Y D, Kwon O H, Lee H S, Kim P, J Microbiol Biotechnol, 2007, 17 (9): 1579-1584) reported that ALA synthetase from *Rhodobacter sphaeroides* was co-expressed in *E. coli* with NADP-dependent malic-enzyme of the *E. coli* itself, and under anaerobic conditions, ALA yield can be improved in an enriched medium without adding succinic acid. However, in terms of improvement degree of ALA, the overall yield is still low, and can not meet production requirements. In Kang et al. (Kang Z, Wang Y, Gu P, Wang Q, Qi Q, Metab Eng, 2011, 13 (5): 492-498), optimized C5 pathway was used and ALA transporters was expressed in *E. coli*. And in a 5 L fermentor, 4.13 g/L of ALA yield can be obtained, and ALA can be produced through fermentation by using a synthetic medium with glucose as being the main carbon source. However, the fermentation period is long, and glucose conversion rate is low, which is only 0.168 g/g (molar ratio of about 0.23). In the above studies, some effort have been made to intracellular supply of the substrate for synthesizing ALA, however, the overall effect is not good. Therefore, till now, exogenous addition are generally used for the supply of substrates for synthesizing ALA, especially for the most commonly used C4 synthetic pathway in the synthesis of ALA. No report can be found that ALA can be produced through fermentation by using engineered strains with C4 pathway in a medium containing glucose, which is cheap, as the main carbon source.

Summing up, it is urgent to develop an efficient, low-cost, low-pollution preparation method for ALA.

SUMMARY

One object of the present invention is to provide a method for constructing 5-aminolevulinic acid high-yield strains and the obtained strains.

In the first aspect, the present invention provides a method for constructing a 5-aminolevulinic acid producing strain, the method comprising:

enhancing the activity of relevant enzymes promoting the synthesis of oxaloacetate in the 5-aminolevulinic acid producing strain, or introducing exogenous relevant enzymes promoting the synthesis of oxaloacetate, and/or attenuating the activity of relevant enzymes in downstream metabolic pathway of succinyl coenzyme A in the 5-aminolevulinic acid producing strain.

In a specific embodiment, the relevant enzyme promoting the synthesis of oxaloacetate is phosphoenolpyruvate carboxylase or pyruvate carboxylase, and the relevant enzyme in downstream metabolic pathway of succinyl coenzyme A is succinyl coenzyme A synthetase or succinate dehydrogenase.

In a preferred embodiment, the enhancement of activity of relevant enzymes promoting the synthesis of oxaloacetate in the 5-aminolevulinic acid producing strain can be achieved by one of the following methods or a combination thereof: enhancing the activity of phosphoenolpyruvate carboxylase, and/or enhancing the activity of pyruvate carboxylase.

In another preferred embodiment, the enhancement of activity of phosphoenolpyruvate carboxylase or pyruvate carboxylase can be achieved by one of the following methods or a combination thereof: expressing homologous or heterologous encoding gene of phosphoenolpyruvic pyruvate carboxylase or pyruvate carboxylase, and/or increasing the number of copies of the encoding gene, and/or modifying the promoter of the encoding gene to enhance transcription initiation rate, and/or modifying the translational regulatory region of messenger RNA carrying the coding gene to increase translational strength.

In a preferred embodiment, "attenuating" includes deleting the relevant enzyme in downstream metabolic pathway of succinyl coenzyme A.

In another preferred embodiment, the relevant enzyme in downstream metabolic pathway of succinyl coenzyme A is succinyl coenzyme A synthetase or succinate dehydrogenase.

In a preferred embodiment, the attenuating of the activity of relevant enzymes in downstream metabolic pathway of succinyl coenzyme A in the 5-aminolevulinic acid producing strain can be achieved by one of the following methods or a combination thereof: knocking out part or all of the encoding gene of succinyl-coenzyme A synthetase or succinate dehydrogenase, gene inactivation via mutation, modifying promoter or translational regulatory region to attenuate the transcription or translation thereof, changing gene sequence to attenuate the stability of mRNA or the stability of the enzyme structure.

In another preferred embodiment, the method further comprises enhancing the synthesis pathway of 5-aminolevulinic acid in the 5-aminolevulinic acid producing strain or introducing exogenous synthesis pathway of 5-aminolevulinic acid.

In a preferred embodiment, the enhancement of the synthesis pathway of 5-aminolevulinic acid in the 5-aminolevulinic acid producing strain refers to the enhancement of the activity of 5-aminolevulinic acid synthetase in the 5-aminolevulinic acid-producing strain or introducing exogenous 5-aminolevulinic acid synthetase.

In another specific embodiment, the method comprises enhancing the activity of 5-aminolevulinic acid synthetase or introducing exogenous 5-aminolevulinic acid synthetase, enhancing the activity of phosphoenolpyruvate carboxylase and knocking out succinyl dehydrogenase in the 5-aminolevulinic acid producing strain.

In another preferred embodiment, the method further comprises determining the yield of 5-aminolevulinic acid in the obtained strain.

In another preferred embodiment, by using the 5-aminolevulinic acid producing strain obtained by said method, 5-aminolevulinic acid can be produced at high-level without exogenously adding succinic acid.

In another preferred embodiment, by using the 5-aminolevulinic acid producing strain obtained by said method, 5-aminolevulinic acid can be produced under aerobic conditions, at high-level and without exogenously adding succinic acid.

In another specific embodiment, said strain itself can synthesize 5-aminolevulinic acid.

In another specific embodiment, the method of the present invention further comprises attenuating the activity of phosphoenolpyruvate carboxykinase and/or malic enzyme.

In a preferred embodiment, attenuating the activity of phosphoenolpyruvate carboxykinase and/or malic enzyme is achieved by knocking out the gene of phosphoenolpyruvate carboxykinase and/or malic enzyme.

In another aspect, the present invention provides a method for constructing a 5-aminolevulinic acid producing strain, the method comprising: attenuating the activity of phosphoenolpyruvate carboxykinase and/or malic enzyme in the 5-aminolevulinic acid producing strain; and enhancing the synthesis pathway of 5-aminolevulinic acid in the 5-aminolevulinic acid producing strain or introducing exogenous synthesis pathway of 5-aminolevulinic acid.

In the second aspect, the present invention provides a 5-aminolevulinic acid producing strain, wherein, in said strain, the activity of relevant enzymes promoting the synthesis of oxaloacetate is enhanced or exogenous relevant enzymes promoting the synthesis of oxaloacetate are introduced, and/or the activity of relevant enzymes in downstream metabolic pathway of succinyl coenzyme A is attenuated.

In a specific embodiment, the relevant enzyme promoting the synthesis of oxaloacetate is phosphoenolpyruvate carboxylase or pyruvate carboxylase, and the relevant enzyme in downstream metabolic pathway of succinyl coenzyme A is succinyl coenzyme A synthetase or succinate dehydrogenase.

In another specific embodiment, the synthesis pathway of 5-aminolevulinic acid in said strain is enhanced. In a preferred embodiment, in said strain, the activity of 5-aminolevulinic acid synthetase is enhanced, or exogenous 5-aminolevulinic acid synthetase is included.

In another specific embodiment, in said strain, the activity of 5-aminolevulinic acid synthetase is enhanced, or exogenous 5-aminolevulinic acid synthetase is included, the activity of phosphoenolpyruvate carboxylase is enhanced, or exogenous phosphoenolpyruvate carboxylase is included and succinate dehydrogenase is knocked out.

In another specific embodiment, said strain is selected from *Escherichia coli, Corynebacterium glutamicum, Rhodobacter sphaeroides, Rhodopseudomonas palustris*, etc.

In another specific embodiment, the activity of phosphoenolpyruvate carboxykinase and/or malic enzyme in said strain is attenuated.

In a preferred embodiment, the gene of phosphoenolpyruvate carboxykinase and/or malic enzyme in said strain is knocked out.

In another aspect, the present invention provides a 5-aminolevulinic acid producing strain, wherein the activity of phosphoenolpyruvate carboxykinase and/or malic enzyme in said strain is attenuated; and the synthesis pathway of 5-aminolevulinic acid in said strain is enhanced, or exogenous synthesis pathway of 5-aminolevulinic acid is included.

In the third aspect, the present invention provides a strain of *Escherichia coli* for producing 5-aminolevulinic acid, and said strain is selected from the following group: the strain deposited in China General Microbiological Culture Collection Center with Accession No. CGMCC 6588, or the strain deposited in China General Microbiological Culture Collection Center with Accession No. CGMCC 6589.

In a specific embodiment, 5-aminolevulinic acid can be produced by using said strain without exogenously adding succinic acid.

In another preferred embodiment, the yield of 5-aminolevulinic acid produced by said strain is greater than 7 g/L.

In another preferred embodiment, the glucose conversion rate for producing 5-aminolevulinic acid in said strain is greater than 0.35 (molar ratio), preferably greater than 0.45 (molar ratio), and most preferably greater than 0.5 (molar ratio).

In another preferred embodiment, by using said 5-aminolevulinic acid producing strain, 5-aminolevulinic acid can be produced at high-level without exogenously adding succinic acid.

In another preferred embodiment, by using said 5-aminolevulinic acid producing strain, 5-aminolevulinic acid can be produced under aerobic conditions, at high-level and without exogenously adding succinic acid.

In the fourth aspect, the present invention provides a method for producing 5-aminolevulinic acid, said method comprising:
1) culturing the strain according to the second or third aspect of the present invention, to give 5-aminolevulinic acid; and
2) obtaining 5-aminolevulinic acid from the fermentation system of 1).

In a preferred embodiment, the yield of 5-aminolevulinic acid produced by said method is greater than 7 g/L.

In another preferred embodiment, by using said method, 5-aminolevulinic acid can be produced at high-level without exogenously adding succinic acid.

In the fifth aspect, the present invention provides a method for producing 5-aminolevulinic acid, said method comprising:
1) culturing a 5-aminolevulinic acid producing strain in a medium in the presense of inhibitors of relevant enzymes in downstream metabolic pathway of succinyl coenzyme A, to give 5-aminolevulinic acid; and
2) obtaining 5-aminolevulinic acid from the culture system of 1).

In a preferred embodiment, the relevant enzyme in downstream metabolic pathway of succinyl coenzyme A is succinyl coenzyme A synthetase or succinate dehydrogenase.

In the sixth aspect, the present invention provides the use of the strain according to the second or third aspect of the present invention for producing 5-aminolevulinic acid and/or producing downstream products by using 5-aminolevulinic acid as a precursor.

In a preferred embodiment, the downstream product is heme or vitamin B12 with ALA being used as a precursor.

It should be understood that in the present invention, the technical features specifically mentioned above and below (such as in the Examples) can be combined with each other, thereby constituting a new or preferred technical solution which needs not be individually described.

MODES FOR CARRYING OUT THE INVENTION

Figure 1:
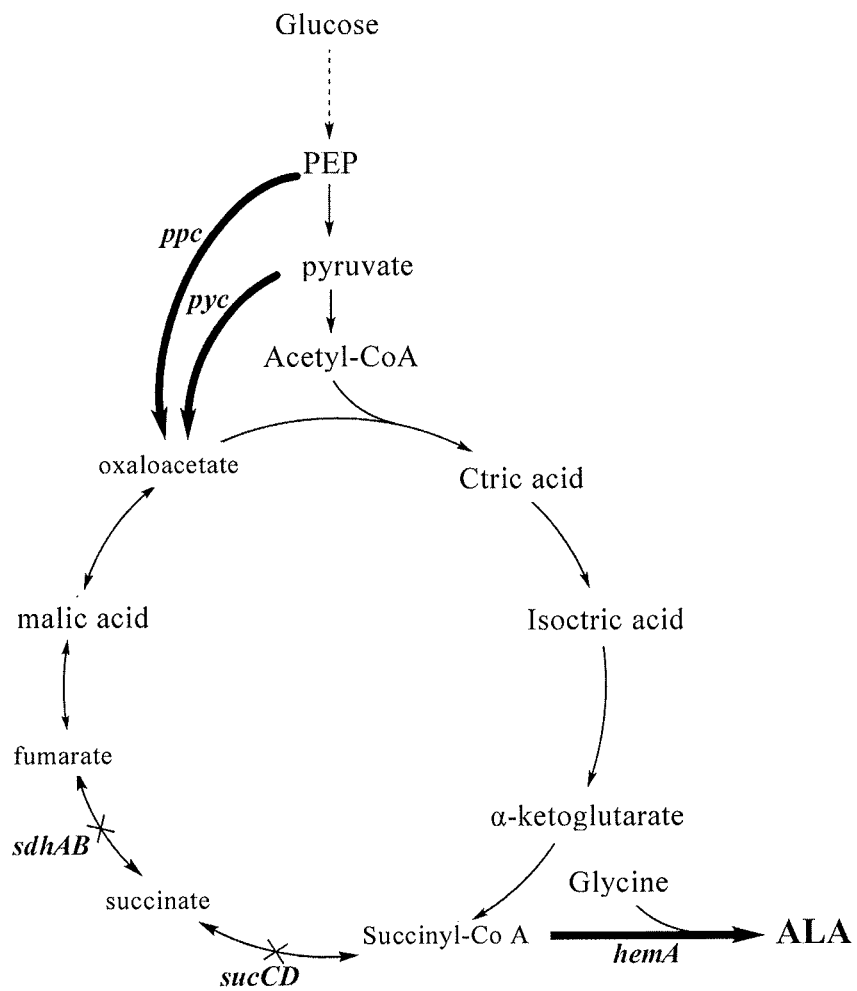
FIG. 1 is a schematic diagram showing the technical solution according to the present invention to improve the yield of ALA.
Figure 2:
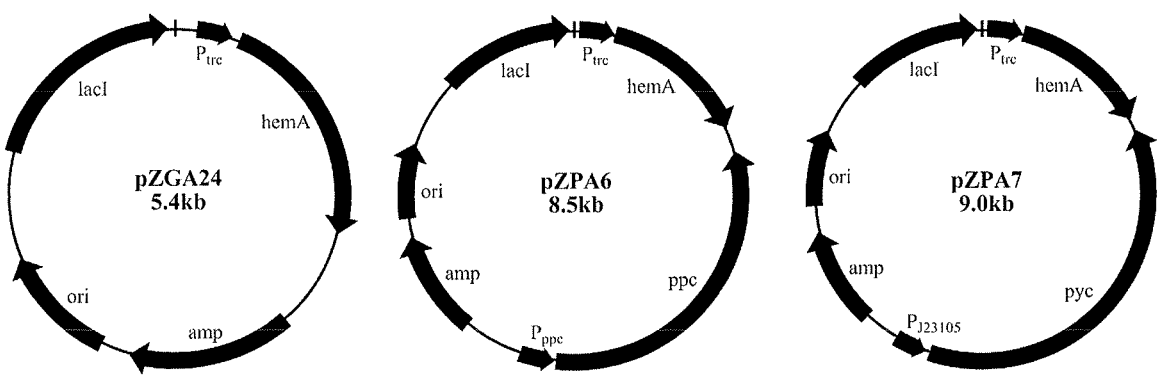
FIG. 2 shows the genetic profiles of the expression vectors used in the present invention.
Figure 3:
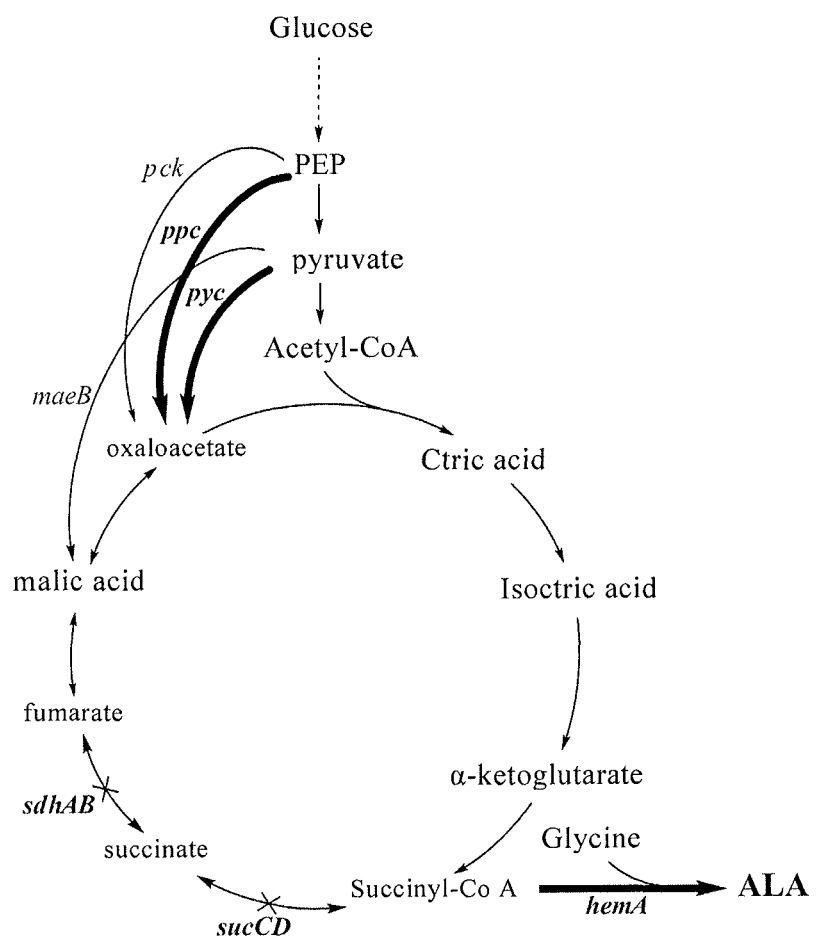
FIG. 3 is a schematic diagram showing another technical solution according to the present invention to improve the yield of ALA.

Through comprehensive and intensive research, the inventors have unexpectedly found that the yield of 5-aminolevulinic acid in a 5-aminolevulinic acid producing strain can be greatly improved by enhancing the activity of relevant enzymes promoting the synthesis of oxaloacetate in said producing strain; the inventors further found that the yield of 5-aminolevulinic acid in said producing strain can also be improved by attenuating the activity of relevant enzymes in downstream metabolic pathway of succinyl coenzyme A in said producing strain; moreover, the inventors found that the yield of 5-aminolevulinic acid can be significantly improved by attenuating the activity of phosphoenolpyruvate carboxykinase and malic enzyme; and the yield of 5-aminolevulinic acid in a obtained producing strain can be further improved by any combination of two or three of the above-mentioned technical means. Based on the above findings, the present invention is completed.

Definition

As used herein, the term "exogenous" refers to such a situation that a system contains a substance that does not originally exist. For example, a gene encoding an enzyme which does not exist in a strain is introduced into the strain by transformation, thereby expressing the enzyme in the strain, accordingly, the enzyme is "exogenous" to the strain.

As used herein, the term "enhancing" refers to increasing, improving, augmenting or raising the activity of a protein, such as enzyme. Based on the teachings of the present invention and the prior art, a person skilled in the art will readily understand that "enhancing" as used herein should also encompass enhancing the activity of an enzyme through expression of heterologous genes encoding the enzyme. In a specific embodiment, the activity of an enzyme can be enhanced by expressing homologous or heterologous encoding gene of the enzyme, and/or increasing the number of copies of the encoding gene, and/or modifying the promoter of the encoding gene to enhance transcription initiation rate, and/or modifying the translational regulatory region of messenger RNA carrying the coding gene to increase translational strength, and/or modifying the encoding gene itself to increase the stability of mRNA or the stability of the protein, or releasing the feedback inhibition of the protein.

Similarly, as used herein, the term "attenuating" refers to reducing, weakening, lowering or eliminating the activity of certain protein, such as enzyme. In a specific embodiment, the activity of an enzyme can be attenuated by knocking out part or all of the encoding gene, gene inactivation or partial inactivation via mutation, modifying promoter or translational regulatory region of a gene to attenuate the transcription or translation thereof, changing gene sequence to attenuate the stability of mRNA or the stability of the enzyme structure.

As used herein, the term "relevant enzymes promoting the synthesis of oxaloacetate" refers to enzymes which are relevant to the synthesis of oxaloacetate, and will exert positive effects, such as promoting, improving, increasing effects, on the synthesis of oxaloacetate. In a specific embodiment, the relevant enzymes promoting the synthesis of oxaloacetate of the present invention include, but are not limited to: phosphoenolpyruvate carboxylase ppc or pyruvate carboxylase pyc. Additionally, based on the teachings of the present invention and the prior art, a person skilled in the art will readily understand that the relevant enzymes promoting the synthesis of oxaloacetate from various origins can be used in the present invention, as long as the enzyme can promote, improve or increase the synthesis of oxaloacetate in strains. In a specific embodiment, phosphoenolpyruvate carboxylase used in the present invention is derived from *Escherichia coli*, and pyruvate carboxylase is derived from rhizobia.

As used herein, the term "relevant enzymes in downstream metabolic pathway of succinyl coenzyme A" refers to an enzyme which uses succinyl coenzyme A as the substrate to synthesize other substances, thereby consuming succinyl coenzyme A. In a specific embodiment, the relevant enzymes in downstream metabolic pathway of succinyl coenzyme A include, but are not limited to: succinyl coenzyme A synthetase or succinate dehydrogenase.

As used herein, the term "the synthesis pathway of 5-aminolevulinic acid" refers to a specific way to produce 5-aminolevulinic acid in microorganisms, including various enzymes, such as 5-aminolevulinic acid synthetase, glutamyl-tRNA synthetase, glutamyl-tRNA reductase or glutamate-1-semialdehyde aminotransferase, and the like. Similarly, as used herein, the expression "enhancing the synthesis pathway of 5-aminolevulinic acid" refers to enhancing the activity of relevant enzymes which involve in the synthesis pathway of 5-aminolevulinic acid, such as 5-aminolevulinic acid synthetase, glutamyl-tRNA synthetase, glutamyl-tRNA reductase or glutamate-1-semialdehyde aminotransferase. In a preferred embodiment, the enzyme is 5-aminolevulinic acid synthetase derived from *Rhodopseudomonas palustris*.

5-Aminolevulinic Acid Producing Strain According to the Present Invention

The present invention provides a 5-aminolevulinic acid producing strain, wherein, in said strain, the activity of relevant enzymes promoting the synthesis of oxaloacetate is enhanced or exogenous relevant enzymes promoting the synthesis of oxaloacetate are included, and/or the activity of relevant enzymes in downstream metabolic pathway of succinyl coenzyme A is attenuated. In a preferred embodiment, the relevant enzymes promoting the synthesis of oxaloacetate include, but are not limited to, phosphoenolpyruvate carboxylase or pyruvate carboxylase; and the relevant enzymes in downstream metabolic pathway of succinyl coenzyme A include, but are not limited to, succinyl-coenzyme A synthetase or succinate dehydrogenase.

In other embodiments, the synthesis pathway of 5-aminolevulinic acid in said strain is enhanced or exogenous synthesis pathway of 5-aminolevulinic acid is included. Accordingly, in a specific embodiment, in the strain according to the present invention, the synthesis pathway of 5-aminolevulinic acid is enhanced or exogenous synthesis pathway of 5-aminolevulinic acid is included, the activity of relevant enzymes promoting the synthesis of oxaloacetate is enhanced or the exogenous relevant enzymes promoting the synthesis of oxaloacetate are included, and/or the activity of relevant enzymes in downstream metabolic pathway of succinyl coenzyme A is attenuated. In a preferred embodiment, in the strain according to the present invention, the activity of 5-aminolevulinic acid synthetase is enhanced, or exogenous 5-aminolevulinic acid synthetase is included, the activity of phosphoenolpyruvate carboxylase is enhanced, or exogenous pyruvate carboxylase is included and succinate dehydrogenase is knocked out.

In a specific embodiment, the activity of phosphoenolpyruvate carboxykinase and/or malic enzyme in the strain according to the present invention is attenuated.

In a preferred embodiment, the gene of phosphoenolpyruvate carboxykinase and/or malic enzyme in the strain according to the present invention is knocked out.

A person skilled in the art will know that many strains can be used to produce 5-aminolevulinic acid. These strains are different, however, the synthesis system, or pathway for synthesizing 5-aminolevulinic acid is similar. Accordingly, based on the teachings of the present invention and the prior art, a person skilled in the art will understand that the strain of the present invention may be any strain which can be used to produce 5-aminolevulinic acid, including but not limited to: *Escherichia coli, Corynebacterium glutamicum, Rhodobacter sphaeroides, Rhodopseudomonas palustris,* and the like.

In a specific embodiment, the present invention provides a strain of *Escherichia coli* deposited in China General Microbiological Culture Collection Center with Accession No. CGMCC 6588. In anther specific embodiment, the present invention provides a strain of *Escherichia coli* deposited in China General Microbiological Culture Collection Center with Accession No. CGMCC 6589.

5-aminolevulinic acid can be produced by using the strain of the present invention without exogenously adding the precursor, succinic acid, and the yield of 5-aminolevulinic acid produced is greater than 7 g/L. Moreover, when using the strain of the present invention to produce 5-aminolevulinic acid, the glucose conversion rate is greater than 0.35 (molar ratio), preferably greater than 0.45 (molar ratio), and most preferably greater than 0.5 (molar ratio). In a preferred embodiment, by using the strain of the present invention, 5-aminolevulinic acid can be produced at high-level without exogenously adding succinic acid. In another preferred embodiment, by using the strain of the present invention, 5-aminolevulinic acid can be produced under aerobic conditions and at high-level, therefore, it is not necessary to alter equipments in the prior art, such as fermentor, so as to facilitate industrial scale-up.

Accordingly, 5-aminolevulinic acid can be readily prepared by using the strain of the present invention at lower cost.

A person skilled in the art will understand that, besides 5-aminolevulinic acid, the strain of the present invention can be also used to produce various downstream products with 5-aminolevulinic acid being used as a precursor. In a specific embodiment, the downstream product is heme or vitamin B12 with ALA being used as a precursor.

The present invention also provides a method for constructing 5-aminolevulinic acid producing strain, the method comprising: enhancing the activity of relevant enzymes promoting the synthesis of oxaloacetate in the 5-aminolevulinic acid producing strain, or introducing exogenous relevant enzymes promoting the synthesis of oxaloacetate, and/or attenuating the activity of relevant enzymes in downstream metabolic pathway of succinyl coenzyme A in the 5-aminolevulinic acid producing strain. In a preferred embodiment, the relevant enzyme promoting the synthesis of oxaloacetate is phosphoenolpyruvate carboxylase or pyruvate carboxylase, and the relevant enzyme in downstream metabolic pathway of succinyl coenzyme A is succinyl coenzyme A synthetase or succinate dehydrogenase.

In a preferred embodiment, the enhancement of activity of relevant enzymes promoting the synthesis of oxaloacetate in the 5-aminolevulinic acid producing strain can be achieved by one of the following methods or a combination thereof: enhancing the activity of phosphoenolpyruvate carboxylase, and/or enhancing the activity of pyruvate carboxylase.

In a further preferred embodiment, the enhancement of activity of phosphoenolpyruvate carboxylase or pyruvate carboxylase can be achieved by one of the following methods or a combination thereof: expressing heterologous encoding gene of phosphoenolpyruvic pyruvate carboxylase or pyruvate carboxylase, and/or increasing the number of copies of the encoding gene, and/or modifying the promoter of the encoding gene to enhance transcription initiation rate, and/or modifying the translational regulatory region of messenger RNA carrying the coding gene to increase translational strength.

In another preferred embodiment, "attenuating" includes deleting the relevant enzyme in downstream metabolic pathway of succinyl coenzyme A. In a further preferred embodiment, the relevant enzyme in downstream metabolic pathway of succinyl coenzyme A is succinyl coenzyme A synthetase or succinate dehydrogenase.

In a preferred embodiment, the attenuating of the activity of relevant enzymes in downstream metabolic pathway of succinyl coenzyme A in the 5-aminolevulinic acid producing strain can be achieved by one of the following methods or a combination thereof: knocking out part or all of the encoding gene of succinyl-coenzyme A synthetase or succinate dehydrogenase, gene inactivation or partial inactivation via mutation, modifying promoter or translational regulatory region of a gene to attenuate the transcription or translation thereof, changing gene sequence to attenuate the stability of mRNA or the stability of the enzyme structure.

In another preferred embodiment, the method further comprises enhancing the synthesis pathway of 5-aminolevulinic acid in the 5-aminolevulinic acid producing strain or introducing exogenous synthesis pathway of 5-aminolevulinic acid. Accordingly, in a specific embodiment, the method comprises enhancing the synthesis pathway of 5-aminolevulinic acid in the 5-aminolevulinic acid producing strain or introducing exogenous synthesis pathway of 5-aminolevulinic acid, enhancing the activity of relevant enzymes promoting the synthesis of oxaloacetate or introducing exogenous relevant enzymes promoting the synthesis of oxaloacetate, and/or attenuating the activity of relevant enzymes in downstream metabolic pathway of succinyl coenzyme A. In a preferred embodiment, the method comprises enhancing the activity of 5-aminolevulinic acid synthetase or introducing exogenous 5-aminolevulinic acid synthetase, enhancing (the activity of) phosphoenolpyruvate carboxylase and knocking out succinyl dehydrogenase in the 5-aminolevulinic acid producing strain.

In another specific embodiment, the method of the present invention further comprises attenuating the activity of phosphoenolpyruvate carboxykinase and/or malic enzyme in the 5-aminolevulinic acid producing strain.

In a preferred embodiment, attenuating the activity of phosphoenolpyruvate carboxykinase and/or malic enzyme is achieved by knocking out the gene of phosphoenolpyruvate carboxykinase and/or malic enzyme.

In a further preferred embodiment, the method further comprises determining the yield of 5-aminolevulinic acid in the obtained strain.

In another preferred embodiment, by using the 5-aminolevulinic acid producing strain obtained by said method, 5-aminolevulinic acid can be produced under aerobic conditions, at high-level and without exogenously adding succinic acid.

Based on the teachings of the present invention and the prior art, a person skilled in the art will understand that, according to the present invention, the capacity of an initial strain for producing 5-aminolevulinic acid was improved by enhancing the activity of relevant enzymes promoting the synthesis of oxaloacetate in the initial strain, or introducing exogenous relevant enzymes promoting the synthesis of oxaloacetate, and/or attenuating the activity of relevant enzymes in downstream metabolic pathway of succinyl coenzyme A in the initial strain, and/or attenuating the activity of phosphoenolpyruvate carboxykinase and/or malic enzyme. Therefore, a method for constructing or modifying a strain by one of, or a combination of two or three of the above technical means for improving the yield of 5-aminolevulinic acid and the obtained strain should fall within the protection scope of the present invention, and the protection scope of the present invention is not limited to the specific methods employed in the Examples and resulting strains.

Based on the method according to the present invention and the resulting strains, the present invention further provides a method for producing 5-aminolevulinic acid, said method comprising: 1) culturing the strain according to the present invention, to give 5-aminolevulinic acid; and 2) obtaining 5-aminolevulinic acid from the fermentation system of 1). In a preferred embodiment, the yield of 5-aminolevulinic acid produced by said method is greater than 7 g/L. In another preferred embodiment, according to said method, it is not necessary to exogenously add succinic acid, and/or it is sufficient to only use glucose as carbon source.

Based on the suggestions and teachings of the present invention, a person skilled in the art will understand that the yield of 5-aminolevulinic acid can also be improved by adding inhibitors of relevant enzymes in downstream metabolic pathway of succinyl coenzyme A into the culture system of a 5-aminolevulinic acid producing strain. In a specific embodiment, the relevant enzyme in downstream metabolic pathway of succinyl coenzyme A is succinyl coenzyme A synthetase or succinate dehydrogenase.

Advantages of the Present Invention:

1. Regarding the strain of the present invention, the glucose conversion rate is improved, and the synthesis of succinyl coenzyme A, which is one of the necessary substrates for synthesizing ALA, is increased, thereby improving the yield of ALA;

2. When preparing ALA by using the strain of the present invention, it is not necessary to exogenously add precursor, succinic acid, therefore, the addition of succinic acid and the use of expensive medium, such as LB, during production are not necessary, thereby greatly reducing the production cost.

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer.

Materials and Methods

DNA polymerase used in Examples of the present invention was purchased from Fastpfu of TransGen Biotech (Beijing); and restriction enzymes and DNA ligase were purchased from Fermentas;

Yeast extract and peptone were purchased from Oxoid (British); glycine and IPTG were purchased from Promega;

5-ALA and p-dimethylaminobenzaldehyde were purchased from Sigma; agar powder and antibiotics were purchased from Solarbio (Beijing); and glucose, acetic acid, perchloric acid, trichloroacetic acid, acetyl acetone, chloroform, and other common chemical reagents were purchased from Sinopharm.

Plasmid extraction kit and agarose gel electrophoresis extraction kit were purchased from Sangon Biotech (Shanghai) Co.,Ltd., and operated in accordance with manufacturer's instructions;

Construction and sequencing of plasmids were performed by BGI;

DH5α competent cells were purchased from TransGen Biotech (Beijing).

Composition of LB medium: yeast extract 5 g/L, peptone 10 g/L, NaCl 10 g/L, solid medium supplemented with 2% agar.

Concentration of antibiotic: ampicillin 100 μg/mL, kanamycin 30 μg/mL.

Detection of ALA: 100 μL sodium acetate buffer (pH 4.6) was added into 200 μL diluted fermentation broth, followed by addition of 5 μL of acetylacetone, incubated in a water bath at 100° C. for 15 min, cooled to room temperature. And then an equal volume of Ehrlish's reagent (42 mL of ice acetic acid, 8 mL 70% perchloric acid, 1 g dimethylamino benzaldehyde) was added and mixed to uniformity. Upon developing for 10 mins, absorbance at 553 nm wavelength was measured.

SBA-40D biosensor analyzer (Shandong Academy) was used to perform Glucose Analysis.

EXAMPLE 1

Construction of Succinyl-Coenzyme A Synthetase Deletion Mutant and Succinate Dehydrogenase Deletion Mutant Genes of E. coli were knocked out through classic Red recombination method (see relevant literatures) as follows: For knocking out succinyl coenzyme A synthetase structural gene sucCD gene, firstly, primers sucCD-1 and sucCD-2, the specific sequence of which can be found in the sequence listing of primer, were designed according to genome sequence of E. coli MG1655 published by NCBI and the sequence of auxiliary vector pKD13, and Kan resistance gene fragment with upstream and downstream homology arms of sucCD gene was amplified by using pKD13 as the template. PCR amplification parameters were listed as follows: 94° C. 2 mins; 94° C. 20 s, 64° C. 20 s, 72° C. 1 min, 30 cycles; 72° C. extension 5 mins. PCR product was recovered from gel, and MG1655/pKD46 strain was transformed by electroporation with the product, wherein the preparation and transformation of competent cells were performed according to J. Sambrook et al. "Molecular Cloning: A Laboratory Manual". Transformants were PCR-verified by using sucCD-3 and sucCD-4 primers, and the size of the fragment from wild-type strain was 2267 bp, while the size of the target band from the sucCD-gene deleted strain was 1558 bp. sucCD-deletion mutant was selected according to the size of band and named as ZPEcA1.

For knocking out sdhAB, firstly, primers sdhAB-1 and sdhAB-2 were designed according to genome sequence of E. coli MG1655 published by NCBI and the sequence of auxiliary vector pKD 13, and Kan resistance gene fragment with upstream and downstream homology arms of sdhAB gene was amplified by using pKD13 as the template. PCR amplification parameters were listed as follows: 94° C. 2 mins; 94° C. 20 s, 64° C. 20 s, 72° C. 1 min, 30 cycles; 72° C. extension 5 mins. PCR product was recovered from gel, and MG1655/pKD46 strain was transformed by the product, wherein the preparation and transformation of competent cells were performed according to J. Sambrook et al. "Molecular Cloning: A Laboratory Manual". Transformants were PCR-verified by using sdhAB-3 and sdhAB-4 primers, and the size of the fragment from wild-type strain was 2553 bp, while the size of the target band from the sucCD-gene deleted strain was 1408 bp. sdhAB-deletion mutant was selected according to the size of band and named as ZPEcA2.

EXAMPLE 2

Construction of Phosphoenolpyruvate Carboxylase ppc and ALA Synthetase Co-Expression Plasmid Primers ppc-F and ppc-R were designed according to genome sequence of E. coli MG1655 published by NCBI, and ppc gene fragment with promoter of the gene was PCR-amplified by using genome of E. coli MG1655 as the template. PCR amplification parameters were listed as follows: 94° C. 2 mins; 94° C. 20 s, 60° C. 20 s, 72° C. 1.5 mins, 30 cycles; 72° C. extension 5 mins. ppc gene fragment was recovered, and treated with HindIII, and the plasmid pZGA24 containing ALA synthetase gene (construction of pZGA24 can be found in: Guo, Xiaofei et al., Synthesis of 5-aminolevulinic acid by using 5-aminolevulinic acid dehydratase deleted recombinant E. coli, Journal of Tianjin University of Science and Technology, 2012, 27(4): 1-6) was also treated with HindIII. The vector and fragment were recovered and ligated by using T4 ligase. DH5α competent cells were transformed by the ligated product, and plated on LB plates containing Amp. Positive clones were selected, and plasmids were extracted and verified through restriction enzyme digestion. Upon sequencing, the correct recombinant plasmid was named as pZPA6.

EXAMPLE 3

Construction of Pyruvate Carboxylase pyc and ALA Synthetase Co-Expression Plasmid Primers pyc-1 and pyc-2 were designed according to the sequence of promoter BBa_J23105 disclosed in BioBrick and genome sequence of Rhizobia CFN42 published by NCBI, and pyc gene fragment with the sequence of constitutive promoter was PCR-amplified by using genome of Rhizobia CFN42 as the template. PCR amplification parameters were listed as follows: 94° C. 2 mins; 94° C. 20 s, 60° C. 20 s, 72° C. 2 mins, 30 cycles; 72° C. extension 5 mins. The target fragments were recovered, and then treated with phosphatase. pWSK29 vector was treated with restriction enzyme PvuII, and then treated with phosphatase. The obtained vector fragment and were ligated by using T4 ligase. DH5α competent cells were transformed by the ligated product, and plated on LB plates containing Amp. Positive clones were selected, and plasmids were extracted and verified through restriction enzyme digestion. Upon sequencing, the correct recombinant plasmid was named as pSLS33.

Primers pyc-F and pyc-R, the specific sequence of which can be found in the sequence listing of primer, were designed according to the sequence of pSLS33 as said above, and pyc gene fragment with the constitutive promoter was amplified by using pSLS33 as the template. PCR amplification parameters were listed as follows: 94° C. 2 mins; 94° C. 20 s, 60° C. 20 s, 72° C. 2 mins, 30 cycles; 72° C. extension 5 mins. Primers pA-1 and pA-2 were designed according to the sequence of pZGA24 vector, and pTrc-hemA vector with ALA synthetase gene was amplified through inverse-PCR by using pZGA24 as the template. PCR amplification parameters were listed as follows: 94° C. 2 mins; 94° C. 20 s, 60° C. 20 s, 72° C. 3 mins, 30 cycles; 72° C. extension 5 mins. pyc gene fragments were recovered, and then treated with endonuclease SmaI, and ligated to pZGA24 vector, which was amplified through inverse-PCR and purified, by using T4 ligase. DH5α competent cells were transformed by the ligated product, and plated on LB plates containing Amp. Positive clones were selected, and plasmids were extracted and verified through restriction enzyme digestion. Upon sequencing, the correct recombinant plasmid was named as pZPA7.

with Amp resistance. After cultured overnight, positive clones were selected, and plasmids were extracted and verified. Recombinant strains MG1655/pZGA24, ZPEcA1/pZGA24, ZPEcA2/pZGA24, MG1655/pZPA6, ZPEcA1/pZPA6, ZPEcA2/pZPA6, MG1655/pZPA7, ZPEcA1/pZPA7 and ZPEcA2/pZPA7 were obtained respectively.

A single colony of the above recombinant strains was inoculated into 5 mL of LB liquid medium containing 100 µg/mL ampicillin, and cultured at 37° C., 220 rpm for 12 hrs. The seed liquid was transferred into a 250 mL flask containing 50 mL of fermentation medium at initial OD 0.05, and cultured at 37° C., 220 rpm for 2.5 hrs. And then a final concentration of 25 µM of IPTG was added. After induced and cultured for 19 hrs, the fermentation liquid was collected, and the concentration of ALA was determined. The fermentation medium was M9 medium supplemented with minor amount of yeast extract, wherein the major components were: $Na_2HPO_4 \cdot 12H_2O$ 12.8 g/L, $KH_2PO_4$ 3.0 g/L,

TABLE 1

Sequence Listing 1 of Primer

| Name of Primer | Sequence of primer |
|---|---|
| sucCD-1 | *GGTCTACGGTTTAAAAGATAACGATTACTGAAGGATGGACAGAACACATG*ATTCCGGGGAT CCGTCGACC(SEQ ID NO: 1) |
| sucCD-2 | *CGGCGAGGGCTATTTCTTATTACAGATATTTATTTCAGAACAGTTTTCAG*TGTAGGCTGGAG CTGCTTCG(SEQ ID NO: 2) |
| sucCD-3 | GTTTAACGTGTCTTATCAGGCCT(SEQ ID NO: 3) |
| sucCD-4 | CGAAAATCATCGCGATAAGCACA(SEQ ID NO: 4) |
| sdhAB-1 | *CTGGTGGTTTACGTGATTTATGGATTCGTTGTGGTGTGGGTGTGTGATG*ATTCCGGGGAT CCGTCGACC(SEQ ID NO: 5) |
| sdhAB-2 | *ACGGTTTACGCATTACGTTGCAACAACATCGACTTGATATGGCCGATGGC*TGTAGGCTGGA GCTGCTTCG(SEQ ID NO: 6) |
| sdhAB-3 | TTATGGATTCGTTGTGGTGTGGGT(SEQ ID NO: 7) |
| sdhAB-4 | TGCGCGTCTTATCAGGCCTA(SEQ ID NO: 8) |
| ppc-F | CCGC<u>AAGCTT</u>TATCCGACCTACACCTTTGGT(SEQ ID NO: 9) |
| ppc-R | CCGC<u>AAGCTT</u>GGACTTCTGTGGAATGCATAGT(SEQ ID NO: 10) |
| pyc-1 | TTTACGGCTAGCTCAGTCCTAGGTACTATGCTAGCACTAGTGAAAGAGGAGAAATACTAG ATGCCCATATCCAAGATACTC(SEQ ID NO: 11) |
| pyc-2 | AACAGCCTGACTTTACACAATCGG(SEQ ID NO: 12) |
| pyc-F | GATA<u>CCCGGG</u>TTTACGGCTAGCTCAGTCCTAGG(SEQ ID NO: 13) |
| pyc-R | CAAG<u>CCCGGG</u>AACAGCCTGACTTTACACAATCGG(SEQ ID NO: 14) |
| pA-1 | GCGGATGAGAGAAGATTTTCAG(SEQ ID NO: 15) |
| pA-2 | CAAAACAGCCAAGCTTTCAGT(SEQ ID NO: 16) |

Note:
letters in italic and bold form indicate the homology arms, and underlined letters indicate the cleavage sites.

EXAMPLE 4

Construction of Recombinant Strains and Comparison of ALA

Wild-type *E. coli* MG1655 and sucCD-deletion mutant and sdhAB-deletion mutant ZPEcA2 were transformed by recombinant plasmids pZGA24, pZPA6 and pZPA7 constructed as above, respectively, and then plated on LB plates NaCl 0.5 g/L, $NH_4Cl$ 1.0 g/L, $MgSO_4$ 2 mM, $CaCl_2$ 0.1 mM, glucose 10 g/L, yeast extract 2 g/L, glycine 4 g/L, concentration of ampicillin being 100 µg/mL. The determination of ALA and the analysis method for glucose were described in "Materials and Methods".

The yield of ALA for each recombinant strain was shown in Table 2, wherein the yield of ALA for the control strain MG1655/pZGA24 was only 1.06 g/L, the yield of ALA for sucCD- or sdhAB-deleted ZPEcA1/pZGA24 and ZPEcA2/ pZGA24 strains was 1.33 g/L and 1.45 g/L respectively, which, compared with that of the initial strain, increased by 25% and 37% respectively, suggesting that deletion of part or all of the activity of succinyl-coenzyme A synthetase or succinate dehydrogenase in *E. coli* can increase the yield of ALA. In MG1655/pZPA6 strain expressing ppc and MG1655/pZPA7 strain expressing pyc, the yield of ALA was 2.52 g/L and 2 g/L respectively, which was 2.38 times and 1.89 times of that of the initial strain respectively, suggesting that the yield of ALA can be significantly improved by enhancing the activity of relevant enzymes promoting the synthesis of oxaloacetate. While in sucCD- or sdhAB-deleted and pyc- or ppc-overexpressed ZPEcA1/pZPA6, ZPEcA2/pZPA6, ZPEcA1/pZPA7 and ZPEcA2/pZPA7 strain, the yield of ALA was 2.43 g/L, 3.08 g/L, 2.12 g/L and 2.66 g/L respectively, all of which was higher than that of the control strain, suggesting that deletion of sucCD or sdhAB and overexpression of pyc or ppc will have certain synergistic effects, which can promote the biosynthesis of ALA. Among these strains, sdhAB-deleted and ppc-expressed ZPEcA2/pZPA6 exhibited the highest yield of ALA, which was 2.91 times of that of the control strain MG1655/pZGA24, and the highest glucose conversion rate 0.47 (molar ratio), which was 2.57 times of that of the initial strain. When the strains of the present invention were used in fermenters, the yield of ALA was 7 g/L or higher, which is a better level at home. The above experimental results show that the yield of ALA can be significantly improved by the expression of exogenous ALA synthetase in *E. coli* in combination with deletion of part or all of the activity of succinyl-coenzyme A synthetase or succinate dehydrogenase and enhancing the activity of relevant enzymes promoting the synthesis of oxaloacetate.

On Sep. 19, 2012, the above recombinant strains MG1655/pZPA6 and ZPEcA2/pZPA6 have been deposited in China General Microbiological Culture Collection Center (NO.1 West Beichen Road, Chaoyang District, Beijing) with Accession No. CGMCC 6588 and CGMCC 6589.

TABLE 2

Fermentation data of strains in flasks

| Strain | ALA (g/L) | ALA/OD$_{600}$ | glucose conversion rate (molar ratio) |
|---|---|---|---|
| MG1655/pZGA24 | 1.06 | 0.30 | 0.18 |
| ZPEcA1/pZGA24 | 1.33 | 0.35 | 0.23 |
| ZPEcA2/pZGA24 | 1.45 | 0.41 | 0.24 |
| MG1655/pZPA6 | 2.52 | 0.56 | 0.39 |
| ZPEcA1/pZPA6 | 2.43 | 0.65 | 0.37 |
| ZPEcA2/pZPA6 | 3.08 | 0.76 | 0.47 |
| MG1655/pZPA7 | 2.00 | 0.47 | 0.35 |
| ZPEcA1/pZPA7 | 2.12 | 0.40 | 0.36 |
| ZPEcA2/pZPA7 | 2.66 | 0.48 | 0.41 |

EXAMPLE 5

Repeated Verification in Strain BW25113

Construction of the recombinant strain: *E. coli* BW25113 (BW25113, as the control strain, was obtained from CGSC (The Coli Genetic Stock Center, Yale University, U.S.A.)), sucC-deleted mutant JW0717 (JW0717 strain with succinyl coenzyme A synthetase β subunit (sucC) deleted) and sdhA-deleted mutant JW0713 (JW0717 and JW0713 were obtained from Kelio Collection, National BioResource Project *E. coli*, Microbial Genetics Laboratory, National Institute of Genetics 1111 Yata, Mishima, Shizuoka, 411-8540 Japan) were transformed by the above plasmids pZGA24, pZPA6 and pZPA7 respectively, and plated on LB plates with Amp resistance. After cultured overnight, positive clones were picked out, and plasmids were extracted and verified. And recombinant strains BW25113/pZGA24, JW0717/pZGA24, JW0713/pZGA24, BW25113/pZPA6, JW0717/pZPA6, JW0713/pZPA6, BW25113/pZPA7, JW0717/pZPA7 and JW0713/pZPA7 were obtained respectively.

The methods of flask fermentation and detection of ALA and glucose for each recombinant strain were the same as mentioned above, the results of which can be found in Table 3. As can be seen from the table, each recombinant strain is substantially the same as the corresponding MG1655 recombinant strain in the yield and change of ALA. And sdhA-deleted and ppc-expressed JW0713/pZPA7 strain exhibited the highest yield, which the yield of ALA was 3.21 g/L and the glucose conversion rate was 0.56 (molar ratio), suggesting that the method of the present invention are also applicable to other strains of *E. coli*.

TABLE 3

Fermentation data of strains in flasks

| Strain | ALA (g/L) | ALA/OD$_{600}$ | glucose conversion rate (molar ratio) |
|---|---|---|---|
| BW25113/pZGA24 | 1.59 | 0.39 | 0.27 |
| JW0717/pZGA24 | 1.21 | 0.32 | 0.23 |
| JW0713/pZGA24 | 2.23 | 0.49 | 0.38 |
| BW25113/pZPA6 | 3.11 | 0.55 | 0.43 |
| JW0717/pZPA6 | 1.88 | 0.53 | 0.32 |
| JW0713/pZPA6 | 3.08 | 0.74 | 0.52 |
| BW25113/pZPA7 | 2.61 | 0.58 | 0.44 |
| JW0717/pZPA7 | 2.25 | 0.50 | 0.39 |
| JW0713/pZPA7 | 3.21 | 0.72 | 0.56 |

The experimental results show that, by using the method of the present invention, when fermenting the recombinant strains in a medium containing glucose as the main carbon source in flasks, the yield of ALA can reach 3.08 g/L, and the yield of ALA in unit mycelium can reach 0.76 g/L/OD, which is 2.91 times and 2.59 times of that of initial strain respectively, and the glucose conversion rate can reach 0.47 (mol/mol), which is 2.57 times of that of the initial strain. By using the recombinant strains constructed by the method of the present invention and the methods for producing ALA using the strains, the addition of succinic acid and the use of expensive medium, such as LB, are not necessary, thereby having good prospects for industrial application and economic value.

EXAMPLE 6

Construction of Recombinant Strains with Enhanced Phosphoenolpyruvate Carboxykinase and Malic Enzyme Activity and Comparison of ALA Yield According to methods similar to those described in Examples 1-5, recombinant strains with enhanced phosphoenolpyruvate carboxykinase (encoding gene: pck) and malic enzyme (encoding gene: maeB) activity were constructed by the inventors, and the yield of ALA for these strains were detected.

Firstly, using the primers shown in Table 4, encoding gene pck of phosphoenolpyruvate carboxykinase from *E. coli* MG1655 was cloned by a method similar to that in Example 2, and connected to pZGA24 vector. The obtained recombinant plasmid was named as pZPA12.

Secondly, primers maeB-F and maeB-R as shown in Table 4 were designed according to genome sequence of *E. coli* MG1655 published by NCBI. Encoding gene maeB of malate dehydrogenase was obtained by PCR-amplification by using genome of *E. coli* MG1655 as the template. Target fragments were phosphorylated with T4 polynucleotide kinase, and ligated to pZGA24 vector fragments, which were obtained through inverse amplification. Upon transformation, restriction enzyme digestion and sequencing, the correct recombinant plasmid was named as pZPA14.

TABLE 4

Sequence listing of primer 2

| Primer name | Primer sequence |
|---|---|
| pck-F | CCGCAAGCTTGCGTGGTGAATCGATACTTT (SEQ ID NO: 17) |
| pck-R | CCGCAAGCTTTGCCTCCCGTTTTGCTTTCT (SEQ ID NO: 18) |
| maeB-F | CGCGGGATCCAAGGAGATATACATATGGATGACCAGTTAAAACA (SEQ ID NO: 19) |
| maeB-R | CAATGGATCCCTAAACTGCTTACCCTGAAT (SEQ ID NO: 20) |

Note:
underlined letters indicate the cleavage sites.

According to methods similar to that described in Example 4, wild-type *E. coli* MG1655 was transformed with the above constructed recombinant plasmids pZPA12 and pZPA14 respectively, to obtain recombinant strains MG1655/pZPA12 and MG1655/pZPA14. The yield of ALA for each recombinant strain was determined by a method similar to that in Example 4, and the results are shown in the following table 6.

TABLE 6

Fermentation data in flasks

| strain | ALA (g/L) | $OD_{600}$ | glucose conversion rate (molar ratio) |
|---|---|---|---|
| MG1655/pZGA24 | 1.06 | 0.30 | 0.18 |
| MG1655/pZPA12 | 0.57 | 4.20 | 0.10 |
| MG1655/pZPA14 | 0.88 | 3.90 | 0.16 |

As can be seen from the above table, compared with the control strain MG1655/pZGA24, the yield of ALA for engineered strains MG1655/pZPA12 and MG1655/pZPA14 was reduced by 46% and 17%, respectively. The enhancement of phosphoenolpyruvate carboxykinase pck activity does not result in the improvement of ALA yield.

EXAMPLE 7

Influence of Knocking Out pck or maeB Gene on the Yield of ALA

Based on the results of Example 9, the inventors further studied the influence of knocking out pck or maeB gene on the synthesis of ALA.

The co-expression vector pZPA6 of ALAS and PPC was introduced into single-gene deleted strain JW3366 (pck gene deleted strain) and JW2447 (maeB gene deleted strain) obtained from Kelio Collection (National BioResource Project *E. coli*, Microbial Genetics Laboratory, National Institute of Genetics 1111 Yata, Mishima, Shizuoka, 411-8540 Japan), respectively. Upon validation, the correct engineered strains JW3366/pZPA6 and JW2447/pZPA6 were obtained. BW25113/pZPA6 obtained in Example 5 was used as the control, and the above recombinant strains were fermented in fermentation media, in which 15 g/L of glucose and 4 g/L of glycine were initially added, to verify the ability of the strains to produce ALA. After culturing for 12 hrs during the process of fermentation, 5 g/L of glucose and 2 g/L of glycine were supplemented. The results of fermentation can be found in Table 7. For JW3366/pZPA6, after culturing for 25 hrs, the yield of ALA was 4.84 g/L (increased by 29% as compared with the control strain BW25113/pZPA6) and the glucose conversion rate was 0.51 mol/mol (increased by 20.8% as compared with the control strain BW25113/pZPA6); while for JW2447/pZPA6, the yield of ALA was slightly reduced, and the conversion rate was increased by 7.8%.

The results demonstrate that the deletion of pck or maeB gene facilitates the accumulation of ALA. Especially, knock-out of pck gene will facilitate the accumulation of ALA and the improvement of glucose conversion rate.

TABLE 7

Influence of deletion of pck or maeB gene on the accumulation of ALA

| Strain | ALA (g/L) | $OD_{600}$ | glucose conversion rate (molar ratio) |
|---|---|---|---|
| BW25113/pZPA6 | 3.75 | 8.37 | 0.42 |
| JW3366/pZPA6 | 4.84 | 8.71 | 0.50 |
| JW2447/pZPA6 | 3.60 | 7.9 | 0.45 |

EXAMPLE 8

Figure 4:
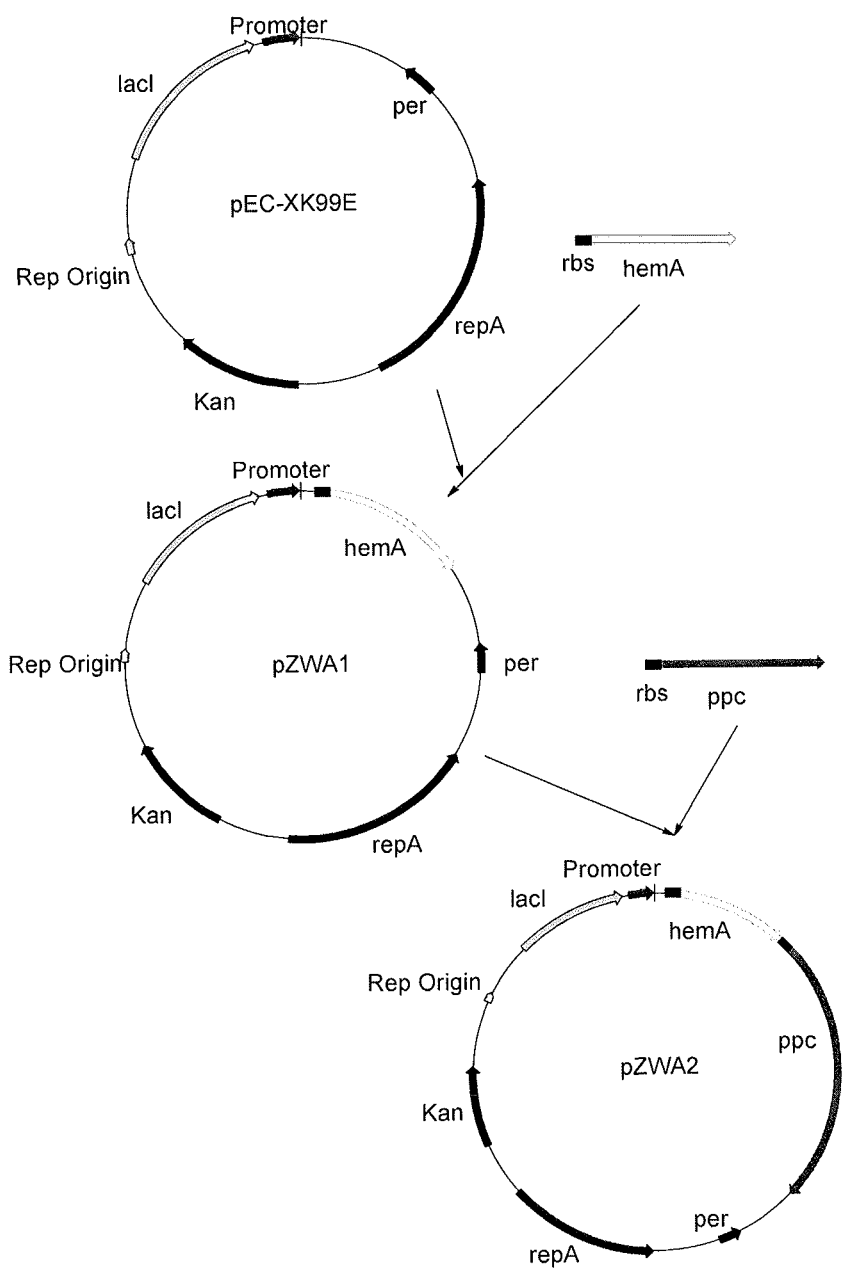
FIG. 4 is a schematic diagram showing the construction of pZWA1 and pZWA2 recombinant vectors.

Construction of Expression Vector for *Corynebacterium glutamicum* and Fermentation Verification Primers hemA-F (primer sequence: GGCGAATTCAAGGAGATATAGATATGAATTACGAAGCCTATTTCCGCCGT; SEQ ID NO: 21) and hemA-R (primer sequence: TATACCCCGGGTCAGGCCGCCTTGGCGAGAC; SEQ ID NO: 22) were designed according to the encoding gene sequence of ALA synthetase from *Rhodopseudomonas palustris* ATCC 17001 published by NCBI (GenBank: JQ048720.1). The target gene hemA was obtained through PCR amplification by using pZGA24 vector as the template (construction of pZGA24 can be found in Guo, Xiaofei et al., Journal of Tianjin University of Science and Technology, 2012, 27(4): 1-6). PCR amplification parameters were listed as follows: 94° C. 10 mins; 94° C. 20 s, 65° C. 30 s, 72° C. 40 s, 30 cycles; 72° C. extension 5 mins. The target fragments were treated with EcoRI and SmaI, and then the obtained fragments were ligated to plasmid pEC-XK99E treated with the same enzymes under the action of DNA ligase. DH5α competent cells were transformed with the ligated products, plated on plates with Kanamycin resistance, and cultured overnight. Positive clones were selected, and the colonies were verified through PCR. Upon verification, the correct transformants were sequenced, and the correct recombinant vector was named as pZWA1 (FIG. 4).

Secondly, Primers Cg-ppc-F (ATACCCCGG-GAAGGAGATATAGATATGACTGATTTTTTACGC-GATGAC; SEQ ID NO: 23) and Cg-ppc-R (GCTCTA-GACTAGCCGGAGTTGCGCAGCGCAGT; SEQ ID NO: 24) were designed according to the sequence of encoding gene ppc for phosphoenolpyruvate carboxykinase from Corynebacterium glutamicum ATCC 13032 published by NCBI (GenBank: BA000036.3). The target gene was obtained through PCR amplification by using the genome of ATCC 13032 as the template. PCR amplification parameters were listed as follows: 94° C. 10 mins; 94° C. 20 s, 65° C. 30 s, 72° C. 2 mins, 30 cycles; 72° C. extension 5 mins. The target fragments were treated with SmaI and XbaI, and then the obtained fragments were ligated to pZWA1 vector treated with the same enzymes under the action of DNA ligase. DH5α competent cells were transformed with the ligated products, plated on plates with Kanamycin resistance, and cultured overnight. Positive clones were selected, and the colonies were verified through PCR. Upon verification, the correct transformants were sequenced, and the correct recombinant vector was named as pZWA2 (FIG. 4).

Corynebacterium glutamicum ATCC 13032 was transformed with the above recombinant vectors pZWA1 and pZWA2 as well as control blank vector pEC-XK99E, so as to obtain recombinant strains ATCC13032/pEC-XK99E, ATCC13032/pZWA1 and ATCC13032/pZWA2.

A single colony of the above recombinant strains was inoculated into 10 mL of LB liquid medium containing 25 μg/mL of kanamycin and 24 g/L of glucose, respectively, and cultured at 30° C., 200 rpm for 12 hrs. The seed liquid was transferred into a 500 mL flask containing 50 mL of fermentation medium at initial OD 0.3, and cultured at 30° C., 200 rpm for 3 hrs. And then a final concentration of 100 μM of IPTG was added. After induced and cultured for 32 hrs, the fermentation liquid was collected, and the concentration of ALA was determined. The composition of fermentation medium in flask was: Glu 50 g/L, $(NH_4)_2SO_4$ 10 g/L, $MnSO_4$ 1 g/L, $K_2HPO_4$ 1.5 g/L, $MgSO_4$ 0.6 g/L, corn syrup 1 g/L, glycine 4 g/L, MOPS 31.395 g/L, pH adjusted to 7.0, and the final concentration of kanamycin was 25 μg/mL. The determination of ALA and the analysis method for glucose were described in "Materials and Methods".

Flask-fermentation results are shown in Table 8. The yield of ALA of ATCC13032/pZWA1 strain only expressing exogenous ALA synthase was 1.31 g/L, and the glucose conversion rate (molar ratio) was 0.052. While in strain ATCC13032/pZWA2, the yield of ALA and the glucose conversion rate were 1.95 g/L and 0.077 respectively, both of which increased by 48% as compared with ATCC13032/pZWA1 strain, thereby demonstrating obvious technical effects. Therefore, the method for modifying ALA producing strains provided by the present invention is also suitable to other microorganisms commonly used in fermentation industry, such as Corynebacterium glutamicum.

TABLE 8

Fermentation data of Corynebacterium glutamicum strains in flasks

| Strain | AlA (g/L) | $OD_{600}$ | glucose conversion rate (molar ratio) |
|---|---|---|---|
| ATCC13032/pEC-XK99E | 0.02 | 18.05 | 0.0008 |
| ATCC13032/pZWA1 | 1.31 | 20.35 | 0.052 |
| ATCC13032/pZWA2 | 1.95 | 23.18 | 0.077 |

Discussion

Based on the synthesis pathway of 5-aminolevulinic acid, the present inventors modified sugar metabolic pathways of host strains through rational design for obtaining ALA-producing recombinant strains. The results demonstrate that the glucose conversion rate and the yield of ALA can be significantly improved by enhancing the activity of relevant enzymes promoting the synthesis of oxaloacetate. In particular, according to the present invention, the yield of ALA and the glucose conversion rate can be significantly improved by expressing phosphoenolpyruvate carboxylase or pyruvate carboxylase to improve anaplerosis of oxaloacetate.

The present inventors further discovered that similar technical effects can be produced by attenuating the activity of relevant enzymes in downstream metabolic pathway of succinyl coenzyme A, i.e., succinyl-coenzyme A synthetase and succinate dehydrogenase. According to the common sense in biology, a multi-subunit enzyme can not exert its complete biological function unless each subunit works together, therefore, any difference in the sequence, structure, or expression level of any subunit will affect the overall activity of the enzyme. Succinyl-coenzyme A synthetase and succinate dehydrogenase are multi-subunit enzyme, wherein succinate coenzyme A synthetase includes two subunits encoded by sucC, sucD respectively, and succinate dehydrogenase includes four subunits encoded by sdhA, sdhB, sdhC and sdhD respectively. In Examples 4 and 5, the inventors confirmed that sucC and sucD, sucC, sdhA and sdhB, sdhA gene deletion will inactivate corresponding enzymes, which in turn facilitates the synthesis of ALA. According to the common sense in biology, it can be anticipated that other genetic modification attenuating the activities of the two enzymes or other methods, such as exogenously adding succinyl-coenzyme A synthetase or succinate dehydrogenase inhibitors, to inhibit or reduce the activities of the two enzymes will facilitate the biosynthesis of ALA.

Glucose conversion rate and the yield of ALA can be further improved by combining the above two strategies. Compared with the control strain only expressing ALA synthetase, the yield of ALA and the glucose conversion rate of the modified strain were increased by 1.91 times and 1.57 times respectively. When the strain of the present invention is used in a fermenter, the yield of ALA can be reach 7 g/L or higher which is a better level. Moreover, the modification method of the present invention can possess better universality, and is also suitable to other microorganisms commonly used in fermentation industry, such as Corynebacterium glutamicum.

Therefore, the yield of ALA and the glucose conversion rate can be significantly improved by the strains and methods provided in the present invention, and the addition of succinic acid and the use of expensive medium, such as LB during the synthesis of ALA, are not necessary, thereby significantly reducing the production cost and having good prospects for industrial application.

Initially, the inventors anticipated that the enhancement of the activity of phosphoenolpyruvate carboxykinase will also improve the synthesis of oxaloacetate, and increase the amount of precursors required for the synthesis of ALA, thereby increasing the yield of ALA. However, the experiments demonstrate that the enhancement of the activity of phosphoenolpyruvate carboxykinase does not produce the expected technical effect. Similarly, the inventors have also found that the enhancement of the activity of malic enzyme can not improve the yield of ALA. Based on further research, the inventors unexpectedly found that attenuating the activity of phosphoenolpyruvate carboxykinase and malic enzyme will significantly increase the yield of ALA. In particular, the deletion of phosphoenolpyruvate carboxykinase can significantly increase the yield of ALA and the glucose conversion rate, and the deletion of malic enzyme will also facilitate to improve the glucose conversion rate.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for producing 5-aminolevulinic acid, the method comprising:

culturing a 5-aminolevulinic acid producing strain in a fermenter, the 5-aminolevulinic acid producing strain being constructed to (1) enhance the activity of phosphoenolpyruvate carboxylase in the 5-aminolevulinic acid producing strain, or introduce exogenous phosphoenolpyruvate carboxylase; and (2) enhance the activity of 5-aminolevulinic acid synthetase in the 5-aminolevulinic acid producing strain, or introduce exogenous 5-aminolevulinic acid synthetase; and obtaining 5-aminolevulinic acid from the fermenter;

wherein the yield of 5-aminolevulinic acid produced by the strain is greater than 7 g/L; and wherein the culturing does not comprise adding exogenous succinic acid to the fermenter.

2. The method according to claim 1, further comprising: attenuating the activity of succinyl coenzyme A synthetase or succinate dehydrogenase.

3. The method according to claim 1, wherein the 5-aminolevulinic acid producing strain is further constructed to (3) attenuate the activity of phosphoenolpyruvate carboxykinase and/or malic enzyme in the 5-aminolevulinic acid producing strain.

4. The method according to claim 3, wherein the 5-aminolevulinic acid producing strain is further constructed to attenuate the activity of malic enzyme in the 5-aminolevulinic acid producing strain.

5. The method according to claim 1, wherein the culturing comprises adding exogenous glycine to the fermenter.

6. The method according to claim 1, wherein the 5-aminolevulinic acid producing strain is an *Escherichia coli* strain, a *Corynebacterium glutamicum* strain, a *Rhodobacter sphaeroides* strain, or a *Rhodopseudomonas palustris* strain.

* * * * *

SEQUENCE LISTING

```
<160> NUMBER OF SEQ ID NOS: 24

<210> SEQ ID NO 1
<211> LENGTH: 70
<212> TYPE: DNA
<213> ORGANISM: Artificial sequence
<220> FEATURE:
<223> OTHER INFORMATION: Primer

<400> SEQUENCE: 1
ggtctacggt ttaaaagata acgattactg aaggatggac agaacacatg attccgggga      60
tccgtcgacc                                                            70

<210> SEQ ID NO 2
<211> LENGTH: 70
<212> TYPE: DNA
<213> ORGANISM: Artificial sequence
<220> FEATURE:
<223> OTHER INFORMATION: Primer

<400> SEQUENCE: 2
cggcgagggc tatttcttat tacagatatt tatttcagaa cagttttcag tgtaggctgg      60
agctgcttcg                                                            70

<210> SEQ ID NO 3
<211> LENGTH: 23
<212> TYPE: DNA
<213> ORGANISM: Artificial sequence
<220> FEATURE:
<223> OTHER INFORMATION: Primer

<400> SEQUENCE: 3
gtttaacgtg tcttatcagg cct                                             23

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4
cgaaaatcat cgcgataagc aca                                             23

<210> SEQ ID NO 5
<211> LENGTH: 70
<212> TYPE: DNA
```

```
<213> ORGANISM: Artificial sequence
<220> FEATURE:
<223> OTHER INFORMATION: Primer

<400> SEQUENCE: 5
ctggtggttt acgtgattta tggattcgtt gtggtgtggg gtgtgtgatg attccgggga     60
tccgtcgacc                                                            70

<210> SEQ ID NO 6
<211> LENGTH: 70
<212> TYPE: DNA
<213> ORGANISM: Artificial sequence
<220> FEATURE:
<223> OTHER INFORMATION: Primer

<400> SEQUENCE: 6
acggtttacg cattacgttg caacaacatc gacttgatat ggccgatggc tgtaggctgg     60
agctgcttcg                                                            70

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
ttatggattc gttgtggtgt ggggt                                           25

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
tgcgcgtctt atcaggccta                                                 20

<210> SEQ ID NO 9
<211> LENGTH: 31
<212> TYPE: DNA
<213> ORGANISM: Artificial sequence
<220> FEATURE:
<223> OTHER INFORMATION: Primer

<400> SEQUENCE: 9
ccgcaagctt tatccgacct acacctttgg t                                    31

<210> SEQ ID NO 10
<211> LENGTH: 32
<212> TYPE: DNA
<213> ORGANISM: Artificial sequence
<220> FEATURE:
<223> OTHER INFORMATION: Primer

<400> SEQUENCE: 10
ccgcaagctt ggacttctgt ggaatgcata gt                                   32

<210> SEQ ID NO 11
<211> LENGTH: 81
<212> TYPE: DNA
<213> ORGANISM: Artificial sequence
<220> FEATURE:
<223> OTHER INFORMATION: Primer
```

<400> SEQUENCE: 11
tttacggcta gctcagtcct aggtactatg ctagcactag tgaaagagga gaaatactag    60
atgcccatat ccaagatact c    81

<210> SEQ ID NO 12
<211> LENGTH: 24
<212> TYPE: DNA
<213> ORGANISM: Artificial sequence
<220> FEATURE:
<223> OTHER INFORMATION: Primer

<400> SEQUENCE: 12
aacagcctga ctttacacaa tcgg    24

<210> SEQ ID NO 13
<211> LENGTH: 33
<212> TYPE: DNA
<213> ORGANISM: Artificial sequence
<220> FEATURE:
<223> OTHER INFORMATION: Primer

<400> SEQUENCE: 13
gatacccggg tttacggcta gctcagtcct agg    33

<210> SEQ ID NO 14
<211> LENGTH: 34
<212> TYPE: DNA
<213> ORGANISM: Artificial sequence
<220> FEATURE:
<223> OTHER INFORMATION: Primer

<400> SEQUENCE: 14
caagcccggg aacagcctga ctttacacaa tcgg    34

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
gcggatgaga gaagattttc ag    22

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
caaaacagcc aagctttcag t    21

<210> SEQ ID NO 17
<211> LENGTH: 30
<212> TYPE: DNA
<213> ORGANISM: Artificial sequence
<220> FEATURE:
<223> OTHER INFORMATION: Primer

<400> SEQUENCE: 17
ccgcaagctt gcgtggtgaa tcgatacttt    30

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
ccgcaagctt tgcctcccgt tttgctttct                              30

<210> SEQ ID NO 19
<211> LENGTH: 44
<212> TYPE: DNA
<213> ORGANISM: Artificial sequence
<220> FEATURE:
<223> OTHER INFORMATION: Primer

<400> SEQUENCE: 19
cgcgggatcc aaggagatat acatatggat gaccagttaa aaca              44

<210> SEQ ID NO 20
<211> LENGTH: 30
<212> TYPE: DNA
<213> ORGANISM: Artificial sequence
<220> FEATURE:
<223> OTHER INFORMATION: Primer

<400> SEQUENCE: 20
caatggatcc ctaaactgct taccctgaat                              30

<210> SEQ ID NO 21
<211> LENGTH: 50
<212> TYPE: DNA
<213> ORGANISM: Artificial sequence
<220> FEATURE:
<223> OTHER INFORMATION: Primer

<400> SEQUENCE: 21
ggcgaattca aggagatata gatatgaatt acgaagccta tttccgccgt        50

<210> SEQ ID NO 22
<211> LENGTH: 31
<212> TYPE: DNA
<213> ORGANISM: Artificial sequence
<220> FEATURE:
<223> OTHER INFORMATION: Primer

<400> SEQUENCE: 22
tataccccgg gtcaggccgc cttggcgaga c                            31

<210> SEQ ID NO 23
<211> LENGTH: 48
<212> TYPE: DNA
<213> ORGANISM: Artificial sequence
<220> FEATURE:
<223> OTHER INFORMATION: Primer

<400> SEQUENCE: 23
ataccccggg aaggagatat agatatgact gattttttac gcgatgac          48

<210> SEQ ID NO 24
<211> LENGTH: 32
<212> TYPE: DNA
<213> ORGANISM: Artificial sequence
<220> FEATURE:
<223> OTHER INFORMATION: Primer

```
<400> SEQUENCE: 24
gctctagact agccggagtt gcgcagcgca gt                                    32
```